(12) United States Patent
Izawa et al.

(10) Patent No.: US 8,395,771 B2
(45) Date of Patent: Mar. 12, 2013

(54) APPARATUS AND METHOD FOR DETERMINING CONCENTRATION OF GASEOUS COMPONENT

(75) Inventors: Jun Izawa, Tokyo (JP); Yasunori Hamano, Tokyo (JP); Nobuhiko Kubota, Tokyo (JP)

(73) Assignee: IHI Corporation, Tokyo (JP)

( * ) Notice: Subject to any disclaimer, the term of this patent is extended or adjusted under 35 U.S.C. 154(b) by 50 days.

(21) Appl. No.: 13/129,374

(22) PCT Filed: Aug. 3, 2009

(86) PCT No.: PCT/JP2009/063724
§ 371 (c)(1),
(2), (4) Date: May 13, 2011

(87) PCT Pub. No.: WO2010/055714
PCT Pub. Date: May 20, 2010

(65) Prior Publication Data
US 2011/0211195 A1    Sep. 1, 2011

(30) Foreign Application Priority Data

Nov. 14, 2008   (JP) ................................ 2008-292075

(51) Int. Cl.
*G01N 21/00* (2006.01)
(52) U.S. Cl. ........................ 356/338; 356/340
(58) Field of Classification Search .......... 356/337–343, 356/432–444; 702/23–24; 250/338.1, 338.5, 250/339.1, 339.11, 339.13, 343, 345; 73/335.01, 73/23.2
See application file for complete search history.

(56) References Cited

U.S. PATENT DOCUMENTS
2007/0097371 A1   5/2007  Parker

FOREIGN PATENT DOCUMENTS

| JP | 54-123997 A | 9/1979 |
| JP | 56-89042 A | 7/1981 |
| JP | 56-90242 A | 7/1981 |
| JP | 63009842 A | 1/1988 |
| JP | 4-151546 A | 5/1992 |
| JP | 11-295217 A | 10/1999 |
| JP | 2003-90796 A | 3/2003 |
| JP | 2004-264048 A | 9/2004 |
| JP | 3699682 B2 | 9/2005 |
| JP | 3861059 B2 | 12/2006 |
| JP | 2007-333518 A | 12/2007 |
| JP | 2008-197185 A | 8/2008 |

OTHER PUBLICATIONS

International Search Report issued in co-pending International Application No. PCT/JP2009/063786, completed Aug. 19, 2009, mailed Sep. 1, 2009.

(Continued)

*Primary Examiner* — Tri T Ton
(74) *Attorney, Agent, or Firm* — Griffin & Szipl, P.C.

(57) ABSTRACT

A light detection value determines concentration of a target component, without using a laser emitter of high laser intensity or a large light collector. By changing orientation of the laser emitter about a horizontal axis, or height of the laser emitter, a laser irradiation position on a ground or water surface is switched between first and second irradiation positions. A photodetector detects first scattered light scattering from the first laser beam at the first irradiation position, second scattered light scattering from the second laser beam at the first irradiation position, third scattered light scattering from the first laser beam at the second irradiation position, and fourth scattered light scattering from the second laser beam at the second irradiation position. A concentration calculator calculates concentration of a target component between the first and second irradiation positions, based on detection values of the first, second, third, and fourth scattered light.

3 Claims, 3 Drawing Sheets

OTHER PUBLICATIONS

International Search Report issued in corresponding International Application No. PCT/JP2009/063724, completed Aug. 31, 2009, mailed Sep. 8, 2009.

Office Action issued in corresponding Australian Patent Application No. 2009315122 dated Oct. 26, 2011.

Office Action issued in related Chinese patent application 200980145331.1 on Dec. 12, 2012.

APPARATUS AND METHOD FOR DETERMINING CONCENTRATION OF GASEOUS COMPONENT

This is a National Phase Application in the United States of International Patent Application No. PCT/JP2009/063724 filed Aug. 3, 2009, which claims priority on Japanese Patent Application No. 2008-292075, filed Nov. 14, 2008. The entire disclosures of the above patent applications are hereby incorporated by reference.

BACKGROUND OF THE INVENTION

1. Technical Field of the Invention

The present invention relates to a gaseous component concentration determination apparatus and method for determining a concentration of a target component in a gas using laser beam.

2. Description of the Related Art

A concentration of a specific target component contained in a gas can be determined in the following manner.

Laser beam having an absorption wavelength $\lambda_1$ unique to the target component is emitted from a laser emitter to the remotely-located gas. Scattered light resulting from scattering of the laser beam of the absorption wavelength $\lambda_1$ by dust in the gas or by the gas itself is detected by a photodetector provided near the laser emitter. In this case, a time of detecting the scattered light by the photodetector differs according to a distance between the laser emitter and a position at which the laser beam is scattered. By converting this time property to a distance property, a detection signal of scattered light from a desired section is obtained. Based on the obtained detection signal, an attenuation rate of light of the wavelength $\lambda_1$ in the section with respect to the laser beam emitting is calculated.

Likewise, laser beam having a non-absorption wavelength $\lambda_2$ of the target component is emitted from the laser emitter to the same remotely-located gas, to calculate an attenuation rate of light of the wavelength $\lambda_2$ in the same section.

A light attenuation rate by the target component can be obtained based on the attenuation rate of light of the wavelength $\lambda_1$ in the section and the attenuation rate of light of the wavelength $\lambda_2$ in the section. Further, the concentration of the target component in the section can be determined from the obtained attenuation rate and known reference data.

Note that Patent Documents 1 and 2 are listed below as prior art documents of this application.
[Patent Document 1] Japanese Patent No. 3861059
[Patent Document 2] Japanese Patent No. 3699682

In the case of detecting the concentration of the target component in the gas in the above-mentioned manner, a very expensive apparatus needs to be used for the following reason.

The light scattered by the dust in the gas or by the gas itself has a very low intensity. Accordingly, it is necessary to use a laser emitter capable of emitting laser beam of a sufficiently high intensity so that the photodetector can detect the scattered light.

However, particularly when emitting the laser beam outdoors, there is a laser intensity constraint for safety reasons. To make up for such a laser intensity, a large, difficult-to-handle, and expensive light collector or the like needs to be used in order to detect weak scattered light.

SUMMARY OF THE INVENTION

The present invention was conceived to solve the conventional problem mentioned above. An object of the present invention is to provide a gaseous component concentration determination apparatus and method that can obtain a sufficiently large light detection value and determine a concentration of a target component in a desired section, without using a laser emitter of a high laser intensity or a large, difficult-to-handle light collector.

To achieve the stated object, according to the present invention, there is provided a gaseous component concentration determination apparatus that emits laser beam into a gas, and detects a concentration of a target component in the gas based on the laser beam passing through the gas, the gaseous component concentration determination apparatus including: a laser emitter that emits first laser beam whose wavelength is a light absorption wavelength of the target component and second laser beam whose wavelength is a non-absorption wavelength of the target component, in an obliquely downward direction so as to be applied to a ground surface or a water surface; a photodetector that detects, in the case where a laser irradiation position on the ground surface or the water surface is switched between a first irradiation position and a second irradiation position by changing an orientation of the laser emitter about a horizontal axis or a height of the laser emitter, first scattered light resulting from scattering of the first laser beam at the first irradiation position, second scattered light resulting from scattering of the second laser beam at the first irradiation position, third scattered light resulting from scattering of the first laser beam at the second irradiation position, and fourth scattered light resulting from scattering of the second laser beam at the second irradiation position; and a concentration calculator that calculates the concentration of the target component between the first irradiation position and the second irradiation position, based on detection values of the first scattered light, the second scattered light, the third scattered light, and the fourth scattered light obtained by the photodetector.

The gaseous component concentration determination apparatus according to the present invention described above calculates the concentration of the target component based on the detection value of light scattered by the ground or water surface, and not based on the detection value of light scattered by the gas. Therefore, it is possible to obtain a sufficiently large light detection value and determine the concentration of the target component in a desired section, without using a laser emitter of a high laser intensity or a large light collector.

That is, since laser beam scattered by the gas is weak, a sufficiently large scattered light detection value for target component concentration calculation cannot be obtained unless a laser emitter of a high laser intensity or a large light collector is used. According to the present invention, however, the ground or water surface is used so that strong light scattered by the ground or water surface is detected. Hence, a sufficiently large scattered light detection value for target component concentration calculation can be obtained to calculate the concentration of the target component in the desired section, without using a laser emitter for emitting high-intensity laser beam or a large light collector.

In addition, merely by changing an orientation of the laser emitter about a horizontal axis or a height of the laser emitter, the section that is subject to the target component concentration determination can be changed easily.

According to a preferred embodiment of the present invention, the first laser beam and the second laser beam are each emitted from the laser emitter to the first irradiation position and the second irradiation position, in a direction that is obliquely downward and also close to a horizontal direction.

This allows a concentration determination error to be ignored as follows. With reference to FIGS. 1 and 4, a distance of the section that is subject to the concentration determination is $L_2-L_1$, but this distance $L_2-L_1$ does not precisely match a distance $L_{1,2}$ between a first irradiation position 5a and a second irradiation position 5b. According to the above preferred embodiment, however, the laser beam is emitted to the first irradiation position 5a and the second irradiation position 5b in a direction that is obliquely downward and also close to a horizontal direction (e.g., a direction that is obliquely downward at an angle of not more than 1 degree from a horizontal plane). Hence, the distance mismatch can be ignored.

Moreover, to achieve the stated object, according to the present invention, there is provided a gaseous component concentration determination method for emitting laser beam into a gas, and detecting a concentration of a target component in the gas based on the laser beam passing through the gas, the gaseous component concentration determination method including: emitting, by a laser emitter, first laser beam whose wavelength is a light absorption wavelength of the target component and second laser beam whose wavelength is a non-absorption wavelength of the target component, in an obliquely downward direction so as to be applied to a ground surface or a water surface; switching a laser irradiation position on the ground surface or the water surface between a first irradiation position and a second irradiation position, by changing an orientation of the laser emitter about a horizontal axis or a height of the laser emitter; detecting, by a photodetector, first scattered light resulting from scattering of the first laser beam at the first irradiation position, second scattered light resulting from scattering of the second laser beam at the first irradiation position, third scattered light resulting from scattering of the first laser beam at the second irradiation position, and fourth scattered light resulting from scattering of the second laser beam at the second irradiation position; and calculating the concentration of the target component between the first irradiation position and the second irradiation position, based on detection values of the first scattered light, the second scattered light, the third scattered light, and the fourth scattered light obtained by the photodetector.

According to the present invention described above, it is possible to obtain a sufficiently large light detection value and determine a concentration of a target component in a desired section, without using a laser emitter of a high laser intensity or a large light collector.

DESCRIPTION OF THE PREFERRED EMBODIMENT

Figure 1:
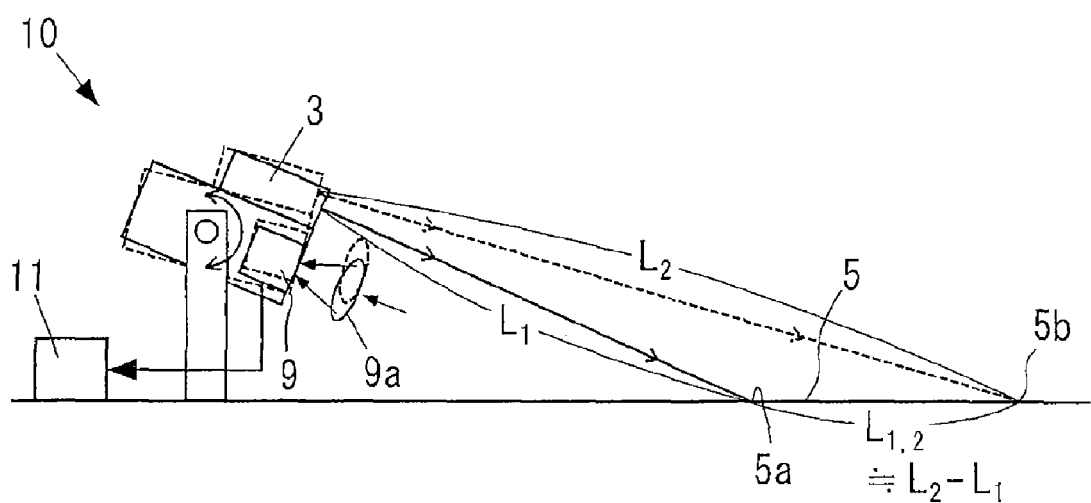
FIG. 1 is a diagram showing a structure of a gaseous component concentration determination apparatus according to a first embodiment of the present invention.

The following describes a best mode for carrying out the present invention, with reference to drawings. Note that common parts in the drawings are given the same reference numerals, and repeated description is omitted.

First Embodiment

FIG. 1 is a diagram showing a structure of a gaseous component concentration determination apparatus 10 according to a first embodiment of the present invention. This gaseous component concentration determination apparatus 10 emits laser beam into a gas, and detects a concentration of a target component in the gas based on the laser beam passing through the gas. For example, the target component is carbon dioxide, ammonia, methane, sulfide gas ($SO_x$) such as sulfur dioxide gas ($SO_2$), or nitrogen oxide gas ($NO_x$) such as nitric oxide (NO).

The gaseous component concentration determination apparatus 10 includes a laser emitter 3, a photodetector 9, and a concentration calculator 11.

The laser emitter 3 emits first laser beam whose wavelength is a light absorption wavelength $\lambda_1$ of the target component and second laser beam whose wavelength is a non-absorption wavelength $\lambda_2$ of the target component, in an obliquely downward direction so as to impinge on a ground or water surface 5. Preferably, the first laser beam has only a wavelength component of the light absorption wavelength $\lambda_1$, whereas the second laser beam includes no component of the light absorption wavelength $\lambda_1$.

As shown in FIG. 1, by changing an orientation of the laser emitter 3 about a horizontal axis, a laser irradiation position on the ground or water surface 5 can be switched between a first irradiation position 5a and a second irradiation position 5b. For instance, the laser emitter 3 is supported by a support so as to be swingable to an arbitrary swinging position about a predetermined horizontal axis. After adjusting or changing the orientation of the laser emitter 3 about the horizontal axis by swinging the laser emitter 3, the laser emitter 3 may be held in a fixed swinging position by an appropriate means. In FIG. 1, solid lines indicate the laser emitter 3 directed toward the first irradiation position 5a, and dashed lines indicate the laser emitter 3 directed toward the second irradiation position 5b. Note that the first irradiation position 5a and the second irradiation position 5b are located remotely (about 1000 m in the example given below) from the laser emitter 3.

Preferably, the first laser beam and the second laser beam are emitted from the laser emitter 3 to the first irradiation position 5a and the second irradiation position 5b, in a direction that is obliquely downward and also close to a horizontal direction. For example, this emission direction is obliquely downward at an angle of not more than 1 degree from a horizontal plane (i.e., the ground or water surface 5). In this case, in FIG. 1, the first laser beam and the second laser beam can be regarded as being emitted horizontally, so that a distance $L_{1,2}$ from the first irradiation position 5a to the second irradiation position 5b can be regarded as $L_{1,2}=L_2-L_1$. As an example, $L_1$ is about 1000 m, and $L_{1,2}$ is 10 m.

The photodetector 9 detects first scattered light resulting from scattering of the first laser beam at the first irradiation position 5a, second scattered light resulting from scattering of the second laser beam at the first irradiation position 5a, third scattered light resulting from scattering of the first laser beam at the second irradiation position 5b, and fourth scattered light resulting from scattering of the second laser beam at the second irradiation position 5b.

The photodetector 9 has a convex lens 9a as a light collector. In this embodiment, the first to fourth scattered light which are relatively high in intensity reach the photodetector 9, and so the convex lens 9a need not be large in size.

Note that the photodetector 9 is fixed to the laser emitter 3, and an orientation of the photodetector 9 about the horizontal axis is changed integrally with the laser emitter 3.

The concentration calculator 11 calculates a concentration of the target component between the first irradiation position 5a and the second irradiation position 5b, based on detection values of the first, second, third, and fourth scattered light obtained by the photodetector 9.

Figure 2:
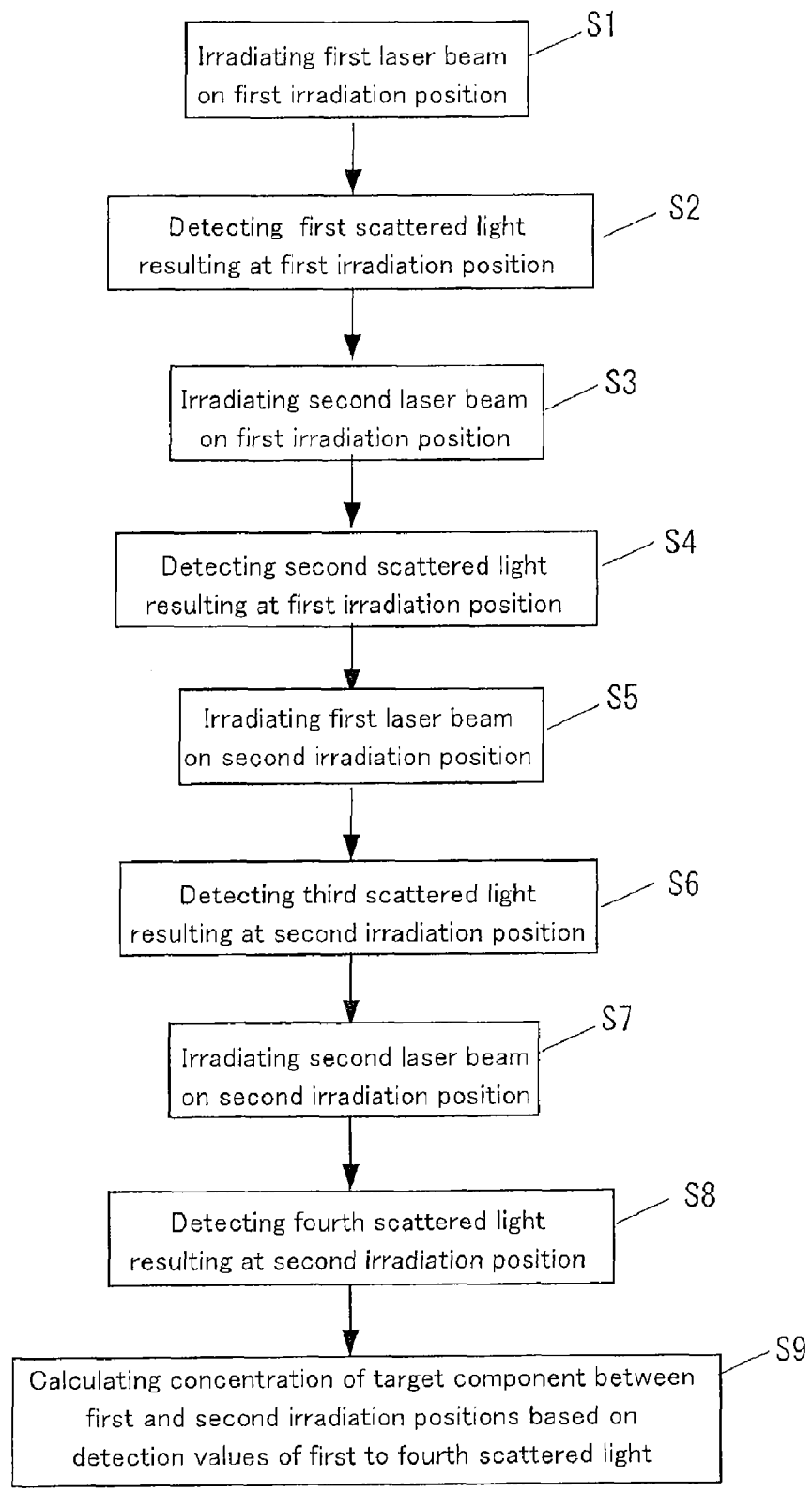
FIG. 2 is a flowchart showing a gaseous component concentration determination method according to the first embodiment of the present invention.

FIG. 2 is a flowchart showing a gaseous component concentration determination method according to the first embodiment of the present invention. This gaseous component concentration determination method is implemented using the gaseous component concentration determination apparatus 10 described above. The operation described above is realized according to this method, though repeated description is omitted.

In step S1, the first laser beam whose wavelength is the light absorption wavelength $\lambda_1$ of the target component is emitted in an obliquely downward direction so as to impinge on the first irradiation position 5a of the ground or water surface 5, using the laser emitter 3. In this example, by setting the orientation of the laser emitter 3 about the horizontal axis to a first orientation, the first laser beam is applied to the first irradiation position 5a on the ground or water surface 5.

In step S2, the first scattered light resulting from scattering of the first laser beam at the first irradiation position 5a is detected by the photodetector 9.

In step S3, in a state where the orientation of the laser emitter 3 about the horizontal axis is maintained at the first orientation, the second laser beam whose wavelength is the non-absorption wavelength $\lambda_2$ of the target component is applied to the first irradiation position 5a by the laser emitter 3.

In step S4, the second scattered light resulting from scattering of the second laser beam at the first irradiation position 5a is detected by the photodetector 9.

In step S5, by setting the orientation of the laser emitter 3 about the horizontal axis to a second orientation, the first laser beam whose wavelength is the light absorption wavelength $\lambda_1$ of the target component is applied to the second irradiation position 5b by the laser emitter 3.

In step S6, the third scattered light resulting from scattering of the first laser beam at the second irradiation position 5b is detected by the photodetector 9.

In step S7, in a state where the orientation of the laser emitter 3 about the horizontal axis is maintained at the second orientation, the second laser beam whose wavelength is the non-absorption wavelength $\lambda_2$ of the target component is applied to the second irradiation position 5b by the laser emitter 3.

In step S8, the fourth scattered light resulting from scattering of the second laser beam at the second irradiation position 5b is detected by the photodetector 9.

In step S9, the concentration of the target component between the first irradiation position 5a and the second irradiation position 5b is calculated based on the detection values of the first, second, third, and fourth scattered light obtained by the photodetector 9.

(Concentration Calculation)

Figure 3:
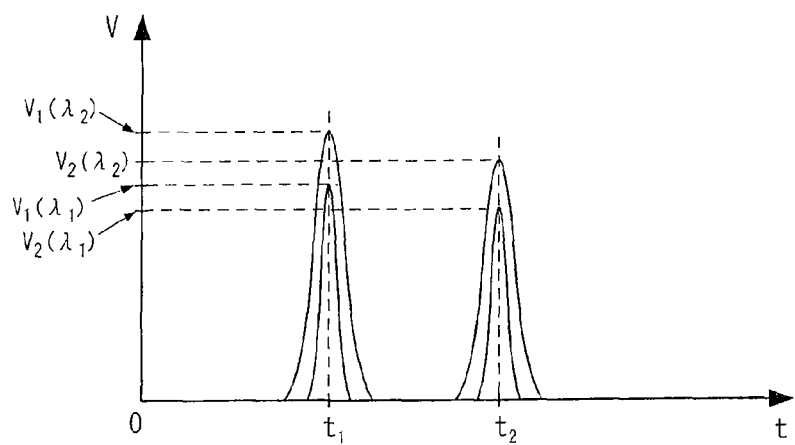
FIG. 3 shows waveforms of detection signals obtained by a photodetector.

FIG. 3 shows detection signals obtained by the photodetector 9. In detail, FIG. 3 is a graph in which the detection signals obtained in steps S2, S4, S6, and S8 mentioned above are overlaid. In FIG. 3, a horizontal axis represents a time, and a vertical axis represents a voltage value proportional to an intensity of each of the above-mentioned first, second, third, and fourth scattered light. The origin 0 of the horizontal axis indicates a point of time at which the first laser beam or the second laser beam is emitted from the laser emitter 3. The detection signals are displayed on a display device (not shown). In FIG. 3, $t_1 = 2L_1/c$, and $t_2 = 2L_2/c$, where c denotes a light speed.

Based on the Lambert-Beer law, the concentration of the target component in the section (i.e., the section indicated by $L_{1,2}$ in FIG. 1) from the first irradiation position 5a to the second irradiation position 5b can be calculated in the following way. In this calculation, it is assumed that the first laser beam and the second laser beam are horizontally emitted as mentioned earlier, and so an approximation of $L_{1,2} = L_2 - L_1$ is made.

First, the following equation (1) holds according to the Lambert-Beer law.

$$T_x(\lambda_x) = T_x' \times \exp\{-2\alpha(\lambda_x) \times N_x \times L_x\} \quad (1)$$

In this equation (1), each character has the following definition.

Subscript x: 1 or 2

$T_x(\lambda_x)$: transmittance of light having a wavelength $\lambda_x$, in the distance $L_1$ or $L_2$ shown in FIG. 1

$T_x'$: transmittance of light due to a factor other than light absorption by the gas, in the distance $L_1$ or $L_2$ shown in FIG. 1

$\alpha(\lambda_x)$: an absorption coefficient of the target component per unit length and unit concentration, for light having the wavelength $\lambda_x$ $N_x$: an average concentration of the target component in a distance $L_x$ $L_x$: the distance $L_1$ or $L_2$ shown in FIG. 1

Here, a light detection intensity of the photodetector 9 is proportional to $T_x(\lambda_x)$. This being so, when E denotes a conversion factor from $T_x(\lambda_x)$ to a voltage, the following equations (2) and (3) hold for $L_1$.

$$V_1(\lambda_1) = E \times T_1' \times \exp\{-2\alpha(\lambda_1) \times N_1 \times L_1\} \quad (2)$$

$$V_1(\lambda_2) = E \times T_1' \times \exp\{-2\alpha(\lambda_2) \times N_1 \times L_1\} \quad (3)$$

Dividing the equation (2) by the equation (3) yields the following equation (4).

$$V_1(\lambda_1)/V_1(\lambda_2) = \exp[-2N_1 L_1 \{\alpha(\lambda_1) - \alpha(\lambda_2)\}] \quad (4)$$

$V_1(\lambda_1)$ and $V_1(\lambda_2)$ can be obtained by measurement by the photodetector 9, and $L_1$, $\alpha(\lambda_1)$, and $\alpha(\lambda_2)$ are known. Hence, by transforming the equation (4), $N_1$ is obtained according to the following equation (5).

$$N_1 = -\ln\{V_1(\lambda_1)/V_1(\lambda_2)\}/2L_1\{\alpha(\lambda_1) - \alpha(\lambda_2)\} \quad (5)$$

Likewise, for $L_2$, $N_2$ is obtained according to the following equation (6).

$$N_2 = -\ln\{V_2(\lambda_1)/V_2(\lambda_2)\}/2L_2\{\alpha(\lambda_1) - \alpha(\lambda_2)\} \quad (6)$$

On the other hand, a concentration Nt of the target component in the desired section is expressed by the following equation (7).

$$Nt = (N_1 \times L_1 - N_2 \times L_2)/(L_2 - L_1) \quad (7)$$

Accordingly, by substituting the equations (5) and (6) and $L_1$ and $L_2$ into the equation (7), the concentration Nt of the target component can be calculated.

Such calculation of the concentration Nt is executed by the concentration calculator 11. That is, the operations of the equations (5) to (7) are executed by the concentration calculator 11.

The gaseous component concentration determination apparatus 10 of the first embodiment described above calculates the concentration of the target component based on the detection value of light scattered by the ground or water surface 5, and not based on the detection value of light scattered by the gas. Therefore, it is possible to obtain a sufficiently large light detection value and determine the concentration of the target component in the desired section, without using a laser emitter of a high laser intensity or a large light collector.

That is, since laser beam scattered by the gas is weak, a sufficiently large scattered light detection value for target component concentration calculation cannot be obtained unless a laser emitter of a high laser intensity or a large light collector is used. According to this embodiment, however, the ground or water surface 5 is used so that strong light scattered by the ground or water surface 5 is detected. Hence, a sufficiently large scattered light detection value for target component concentration calculation can be obtained to calculate the concentration of the target component in the desired section, without using a laser emitter for emitting high-intensity laser beam or a large light collector.

In addition, merely by changing the orientation of the laser emitter 3 about the horizontal axis or a height of the laser emitter 3, the section that is subject to the target component concentration determination can be changed easily.

Moreover, the first laser beam and the second laser beam are emitted from the laser emitter 3 to the first irradiation position 5a and the second irradiation position 5b, in a direction that is obliquely downward and also close to the horizontal direction. This allows a concentration determination error to be ignored as follows. The distance of the section that is subject to the concentration determination is $L_2-L_1$, but this distance $L_2-L_1$ does not precisely match the distance $L_{1,2}$ between the first irradiation position 5a and the second irradiation position 5b. According to this embodiment, however, the laser beam is emitted to the first irradiation position 5a and the second irradiation position 5b in a direction that is obliquely downward and also close to the horizontal direction (e.g., a direction that is obliquely downward at an angle of not more than 1 degree from the horizontal plane). Hence, the distance mismatch can be ignored.

Second Embodiment

Figure 4:
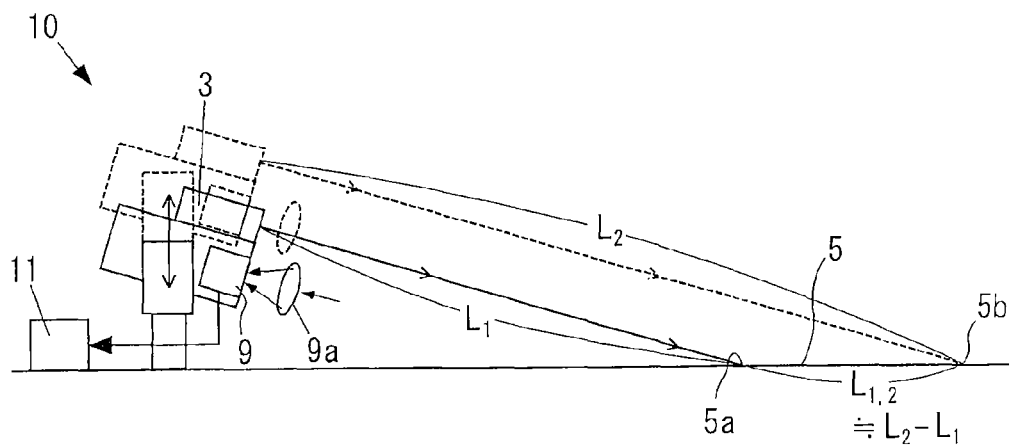
FIG. 4 is a diagram showing a structure of a gaseous component concentration determination apparatus according to a second embodiment of the present invention.

FIG. 4 is a diagram showing a structure of the gaseous component concentration determination apparatus 10 according to a second embodiment of the present invention.

In the second embodiment, instead of changing the orientation of the laser emitter 3 about the horizontal axis, the height of the laser emitter 3 is changed to thereby switch the laser irradiation position on the ground or water surface 5 between the first irradiation position 5a and the second irradiation position 5b. In FIG. 4, solid lines indicate the laser emitter 3 directed toward the first irradiation position 5a, and dashed lines indicate the laser emitter 3 directed toward the second irradiation position 5b.

For example, the laser emitter 3 may be supported by a support so as to be slidable to an arbitrary height in a vertical direction. After adjusting or changing the height of the laser emitter 3, the laser emitter 3 may be held at a fixed height by an appropriate means.

The other structure and operation of the second embodiment and the gaseous component concentration determination method using the gaseous component concentration determination apparatus 10 of the second embodiment are the same as the first embodiment. In detail, in steps S1 and S3 mentioned above, by setting the laser emitter 3 to a first height, the first laser beam and the second laser beam are applied to the first irradiation position 5a on the ground or water surface 5. In addition, in steps S5 and S7 mentioned above, by setting the laser emitter 3 to a second height, the first laser beam and the second laser beam are applied to the second irradiation position 5b on the ground or water surface 5. Moreover, the photodetector 9 is fixed to the laser emitter 3 as in the first embodiment, and so a height of the photodetector 9 is changed integrally with the laser emitter 3.

Though the concentration of the target component in one section between the first irradiation position 5a and the second irradiation position 5b is determined in each of the embodiments described above, the concentration of the target component in two or more sections may also be determined.

In detail, by changing the orientation of the laser emitter 3 about the horizontal axis or the height of the laser emitter 3 in sequence, the laser irradiation position on the ground or water surface 5 is switched in order of the first irradiation position 5a, the second irradiation position 5b, and a third irradiation position. Note that the irradiation position may be switched in any other order. In this case, the photodetector 9 detects fifth scattered light resulting from scattering of the first laser beam at the third irradiation position and sixth scattered light resulting from scattering of the second laser beam at the third irradiation position, in addition to the above-mentioned first to fourth scattered light. The concentration calculator 11 also calculates the concentration of the target component between the second irradiation position 5b and the third irradiation position, based on the detection values of the third, fourth, fifth, and sixth scattered light obtained by the photodetector 9. The same applies to the case of further increasing the number of sections that are subject to the target component concentration determination.

The present invention is not limited to the embodiments described above, and various changes can be made without departing from the scope of the present invention.

The invention claimed is:

1. A gaseous component concentration determination apparatus that emits a laser beam into a gas, and detects a concentration of a target component in the gas based on the laser beam passing through the gas, the gaseous component concentration determination apparatus comprising:
   (a) a laser emitter that emits a first laser beam whose wavelength is a light absorption wavelength of the target component and a second laser beam whose wavelength is a non-absorption wavelength of the target component, in an obliquely downward direction so as to be applied to a ground surface or a water surface;
   (b) a photodetector that detects, in the case where a laser irradiation position on the ground surface or the water surface is switched between a first irradiation position and a second irradiation position by changing an orientation of the laser emitter about a horizontal axis or a height of the laser emitter, first scattered light resulting from scattering of the first laser beam at the first irradiation position, second scattered light resulting from scattering of the second laser beam at the first irradiation position, third scattered light resulting from scattering of the first laser beam at the second irradiation position, and fourth scattered light resulting from scattering of the second laser beam at the second irradiation position; and
   (c) a concentration calculator that calculates the concentration of the target component between the first irradiation position and the second irradiation position, based on detection values of the first scattered light, the second scattered light, the third scattered light, and the fourth scattered light obtained by the photodetector.

2. The gaseous component concentration determination apparatus according to claim 1, wherein the first laser beam and the second laser beam are each emitted from the laser emitter to the first irradiation position and the second irradiation position, in a direction that is obliquely downward and also close to a horizontal direction.

3. A gaseous component concentration determination method for emitting a laser beam into a gas, and detecting a concentration of a target component in the gas based on the laser beam passing through the gas, the gaseous component concentration determination method comprising the steps of:
(a) emitting, by a laser emitter, a first laser beam whose wavelength is a light absorption wavelength of the target component and a second laser beam whose wavelength is a non-absorption wavelength of the target component, in an obliquely downward direction so as to be applied to a ground surface or a water surface;
(b) switching a laser irradiation position on the ground surface or the water surface between a first irradiation position and a second irradiation position, by changing an orientation of the laser emitter about a horizontal axis or a height of the laser emitter;
(c) detecting, by a photodetector, first scattered light resulting from scattering of the first laser beam at the first irradiation position, second scattered light resulting from scattering of the second laser beam at the first irradiation position, third scattered light resulting from scattering of the first laser beam at the second irradiation position, and fourth scattered light resulting from scattering of the second laser beam at the second irradiation position; and
(d) calculating the concentration of the target component between the first irradiation position and the second irradiation position, based on detection values of the first scattered light, the second scattered light, the third scattered light, and the fourth scattered light obtained by the photodetector.

* * * * *